United States Patent
Arabia et al.

(10) Patent No.: US 8,273,009 B2
(45) Date of Patent: Sep. 25, 2012

(54) PIPETTE ASPIRATION DEVICE

(75) Inventors: Dustin John Arabia, New Kensington, PA (US); Chad E. Unger, Verona, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 588 days.

(21) Appl. No.: 12/397,451

(22) Filed: Mar. 4, 2009

(65) Prior Publication Data

US 2009/0227833 A1 Sep. 10, 2009

Related U.S. Application Data

(60) Provisional application No. 61/034,629, filed on Mar. 7, 2008.

(51) Int. Cl.
| | |
|---|---|
| A61B 17/43 | (2006.01) |
| B65B 43/42 | (2006.01) |
| B67C 3/00 | (2006.01) |
| B67D 7/84 | (2010.01) |
| G01F 19/00 | (2006.01) |
| F16L 43/00 | (2006.01) |
| F04F 10/00 | (2006.01) |

(52) U.S. Cl. ........... 600/33; 141/130; 222/160; 73/1.73; 73/1.74; 137/150

(58) Field of Classification Search ............... 141/130; 222/160; 73/1.73, 1.74; 137/150
See application file for complete search history.

(56) References Cited

U.S. PATENT DOCUMENTS

| | | | | |
|---|---|---|---|---|
| 672,207 | A | | 4/1901 | Dunn |
| 902,109 | A | * | 10/1908 | Powell ............................ 433/49 |
| 2,358,936 | A | | 9/1944 | Mathis ............................ 222/192 |
| 3,503,665 | A | * | 3/1970 | Carter ............................ 359/398 |
| 3,834,241 | A | | 9/1974 | Garren et al. ................. 73/425.6 |
| 5,079,170 | A | | 1/1992 | Rosman et al. ................ 436/178 |
| 5,403,745 | A | | 4/1995 | Ollington et al. ............... 435/11 |
| 5,510,083 | A | | 4/1996 | Sack et al. ..................... 422/100 |
| 5,725,831 | A | | 3/1998 | Reichler et al. ................. 422/56 |
| 5,787,799 | A | * | 8/1998 | Mohrhauser et al. ........... 99/345 |
| 5,902,278 | A | * | 5/1999 | Aguilar ........................... 604/227 |
| 6,074,611 | A | | 6/2000 | Flesher ........................... 422/100 |
| 6,589,484 | B2 | | 7/2003 | Buehler ........................... 422/100 |
| 6,838,278 | B2 | | 1/2005 | Fortino ....................... 435/307.1 |
| 6,982,063 | B2 | | 1/2006 | Hamel et al. ................... 422/100 |
| 7,033,543 | B1 | | 4/2006 | Panzer et al. ................... 422/100 |
| 7,094,379 | B2 | | 8/2006 | Fouillet et al. ................. 422/100 |
| 7,204,163 | B2 | | 4/2007 | Uldry et al. ................. 73/864.18 |
| 2005/0142038 | A1 | | 6/2005 | Petrek et al. ................... 422/100 |
| 2006/0217670 | A1 | | 9/2006 | Cecchi et al. .................. 604/209 |
| 2007/0125675 | A1 | | 6/2007 | Booker et al. ................. 206/438 |
| 2007/0239115 | A1 | | 10/2007 | Cecchi ........................... 604/187 |

FOREIGN PATENT DOCUMENTS

| | | |
|---|---|---|
| DE | 12 77 589 B | 9/1968 |
| DE | 42 14 634 C1 | 10/1993 |
| EP | 1 212 138 B1 | 6/2005 |
| WO | WO 2006/030201 A1 | 3/2006 |
| WO | WO 2008/002483 A2 | 1/2008 |

* cited by examiner

*Primary Examiner* — Louise Humphrey

(74) *Attorney, Agent, or Firm* — Brinks Hofer Gilson & Lione

(57) ABSTRACT

A device for aspirating sample media into a pipette for use in a micro-manipulation procedure includes a ring member having an opening sized for receiving a digit of an operator, and an aspirating bulb engaged with the ring member. The aspirating bulb has an open end sized for receiving an end of the pipette, and includes a compressible chamber capable of creating a suction force suitable for aspirating the sample media into the pipette. The aspirating bulb is oriented along the ring member such that the chamber is compressible by a digit on the same hand of the operator as the digit receivable in the ring member.

9 Claims, 4 Drawing Sheets

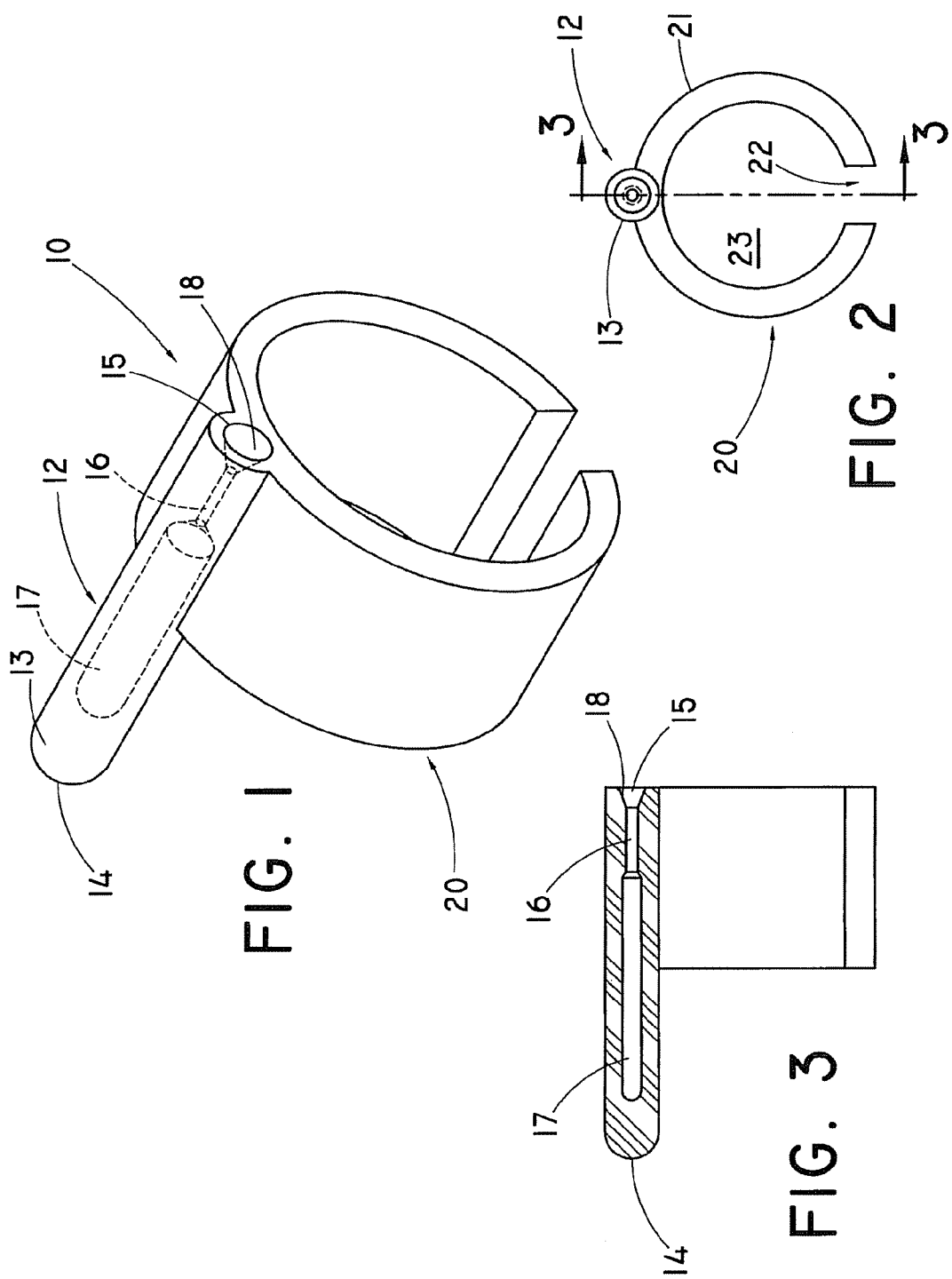

PIPETTE ASPIRATION DEVICE

RELATED APPLICATION

The present patent document claims the benefit of the filing date under 35 U.S.C. §119(e) of Provisional U.S. Patent Application Ser. No. 61/034,629, filed Mar. 7, 2008, which is hereby incorporated by reference.

BACKGROUND

1. Technical Field

The present application relates to a device for use in aspirating biological material, and more particularly, to a device and method for use in aspirating cells from a reservoir through a pipette during micro-manipulation techniques, such as the manipulation of an oocyte cumulus complex or an embryo, or the denuding of an oocyte complex.

2. Background Information

With the continuous advances of modern medicine, there is an ongoing need for increasingly smaller medical appliances, such as pipettes, that are suitable for carrying out medical techniques on a micro scale not previously possible. With the advent of increasingly smaller appliances, there is a corresponding increase in the need for tools or other devices suitable for use in association with the appliances.

As a part of this trend toward micro-medicine, the use of small diameter pipettes that are suitable for aspirating and/or delivering very small cells and/or volumes has dramatically increased. One example of a field of medicine that has experienced an increased use of such micro-size pipettes is the field of fertility treatment. Pipettes used in this field are typically used in micro-treatment techniques, such as in vitro fertilization (IVF) and intracytoplasmic sperm injection (ICSI). These fields, and others, continue to grow as more sophisticated micro-manipulation tools and techniques are developed.

For example, in order to carry out ICSI, a single sperm is directly injected, under microscopic vision, into the cytoplasm of an oocyte. In order to prepare for this injection, the single sperm must be isolated, and aspirated into a microinjection pipette. Another pipette is used to hold the oocyte in position as the sperm is injected into the cytoplasm. Prior to injection, a denuding pipette is used to denude the cumulus mass from the oocyte. It would not be possible to perform such delicate manipulation techniques without the use of reliable micro-scale devices, such as the described pipettes.

Pipettes for aspirating cells for use in micro-manipulation techniques are known in the art. Typically, a bulb is attached to the proximal end of the pipette to supply a suction force sufficient for aspirating the cells from a sample dish through the distal end of the pipette. Many such bulbs comprise rigid or semi-rigid elongated structures that the operator holds in his or her hand in the nature of a pencil. These bulbs are often inconvenient to use, and frequently require the operator to maintain a sufficient suction force (not too small, not too great) on the pipette while holding the bulb at an inconvenient angle. When many samples are to be aspirated, this repetitive action may cause strain to the operator. In addition, it is often difficult to control the amount of sample media aspirated into the pipette.

The pipette can also be attached to a rigid handle design that includes, e.g., a stylet wire that protrudes into the pipette. By actuating the wire up and down, suction force sufficient for aspirating the cells may be created. Additionally, it may be necessary for the operator to use digits (i.e., fingers and/or thumb) on each hand to insure that the pipette is properly positioned, and that a proper amount of suction force can be applied through the bulb.

It is desired to provide a device for use with a pipette that facilitates aspiration procedures practiced in the art. It is particularly desired to provide such a device and a method for use with pipettes suitable for use in micro-manipulation procedures, such as IVF and ICSI.

BRIEF SUMMARY

In one form thereof, the present invention relates to a device for use in aspirating sample media into a pipette. The device includes a ring member having an opening sized for receiving at least one of a digit of an operator, and a substrate capable of being grasped by a hand of the operator. An aspirating bulb is engaged with the ring member. The aspirating bulb has an open end sized for receiving an end of the pipette therein, and includes a compressible chamber capable of creating a suction force suitable for aspirating the sample media into the pipette. The aspirating bulb is oriented along the ring member such that the chamber is compressible by a digit on the same hand of the operator as the digit receivable in the ring member or on the hand that grasps the substrate.

In another form thereof, the invention relates to a method for aspirating sample media from a reservoir into a pipette for carrying out a micro-manipulation procedure. An aspirating device comprising a ring member and a bulb is provided. The ring member has an opening sized for receiving a finger of an operator, or for receiving a substrate capable of being grasped by the operator. The bulb is engaged with a surface of the ring member. The bulb has an open end sized for receiving an end of the pipette therein, and includes a compressible chamber for creating an aspirating force. The finger or the substrate is introduced through the ring member opening, and a first end of the pipette is inserted into the open end of the bulb. The chamber is compressed to create the aspirating force, and a second end of the pipette is inserted into the reservoir of sample media. The compression is at least partially released, and at least a portion of the sample is aspirated into the pipette.

In yet another form thereof, the invention relates to a system for use in carrying out a micro-manipulation procedure. The system includes a pipette sized for receiving a sample media for use in the micro-manipulation procedure, and a device for aspirating the sample media into the pipette. The device comprises a ring member and a bulb engaged with a surface of the ring member. The ring member has an opening sized for receiving at least one of a digit of an operator and a substrate capable of being grasped by an operator carrying out the procedure. The bulb has an open end sized for receiving an end of the pipette, and includes a compressible chamber capable of creating a suction force suitable for aspirating the sample media.

BRIEF DESCRIPTION OF THE DRAWINGS

FIG. 1 is a perspective view of a pipette aspiration device according to an embodiment of the present invention;

FIG. 2 is a view of the distal end of the pipette aspiration device of FIG. 1;

FIG. 3 is a sectional view of a portion of the pipette aspiration device, taken along line 3-3 of FIG. 2;

DETAILED DESCRIPTION OF THE DRAWINGS AND THE PRESENTLY PREFERRED EMBODIMENTS

Figure 4:
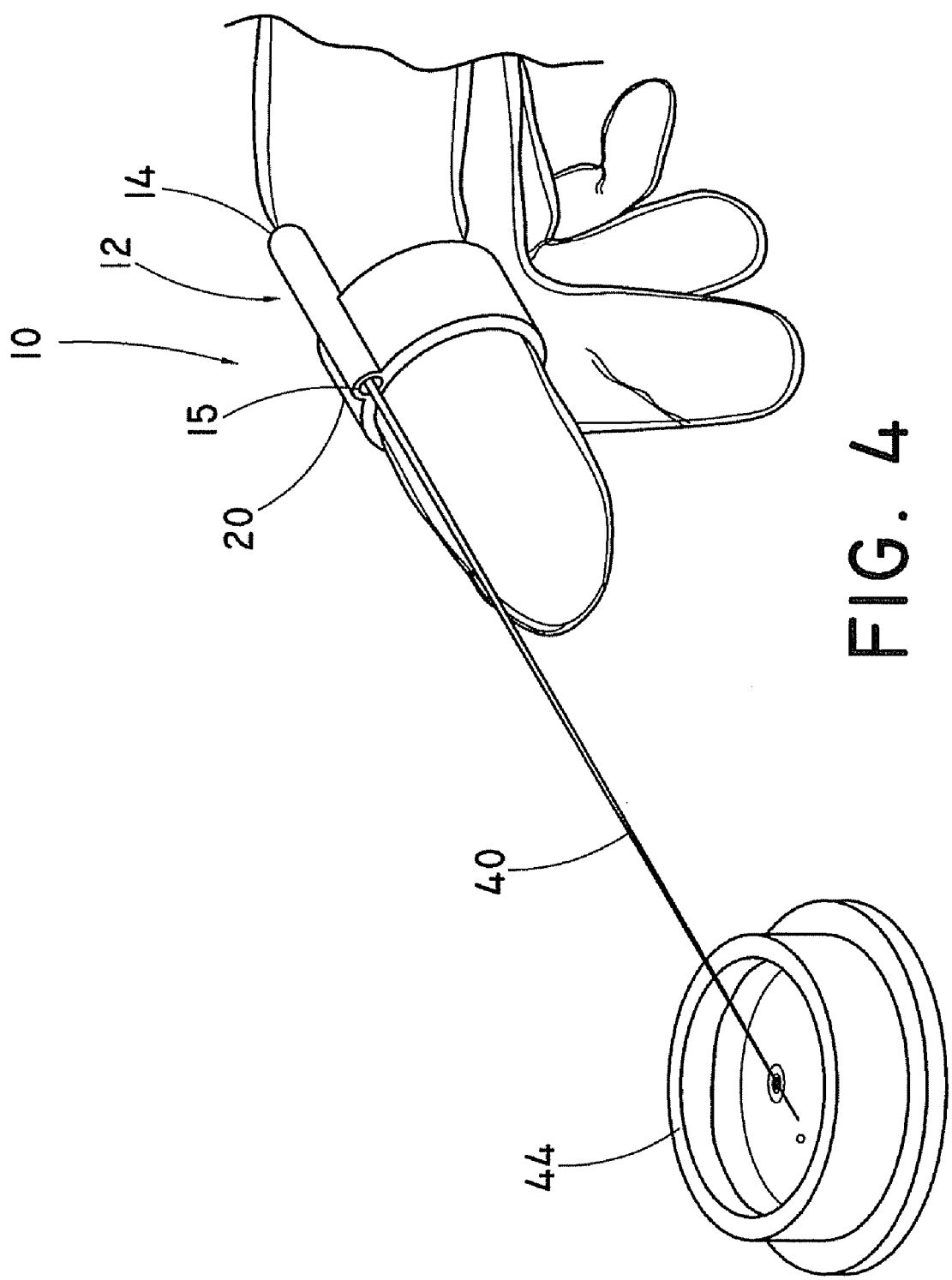
FIG. 4 is a view illustrating one manner of use of the pipette aspiration device of FIG. 1 in aspirating cells from a sample.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the inventive device, as well as the axial ends of various related components. The term "proximal" is used in its conventional sense to refer to the end of the device (or component) that is closest to the operator during use of the device. The term "distal" is used in its conventional sense to refer to the end of the device (or component) that is initially inserted into, or positioned closest to, the media targeted for aspiration (e.g., a sample dish) during use of the device.

The present invention comprises a device suitable for use in aspirating biological sample media, (e.g., biological fluids, cells, or related media) quickly and comfortably utilizing a micro-size medical apparatus, such as a pipette. In a preferred embodiment, the aspiration device comprises a ring member and an aspiration bulb engaged with the ring member. The ring member may be fitted onto a digit (i.e., a thumb or finger) of the operator, such as the index finger. Alternatively, the ring member may be sized for engagement with a device that is suitable for grasping by the operator, such as a pipette holder or container.

The bulb portion of the inventive device may be structured for operation in well-known manner. As well understood by those of skill in the art, compressing a bulb causes fluids to be expelled from the bulb, as well as from an apparatus, such as a pipette, that may be operably engaged with the bulb. When compression on the bulb is released, a suction, or aspirating, force is created for drawing a fluid of interest, such as a sample media, into the pipette. In this manner, sample media may be controllably drawn into the pipette, from which it may be dispensed as desired for carrying out a medical procedure.

Use of the inventive device allows very favorable control of the pipette during the aspiration of a sample. Non-limiting examples of techniques in which the inventive device will find particular utility include IVF and ICSI procedures, such as the manipulation of an oocyte cumulus complex or an embryo, and the denuding of an oocyte (the process of stripping off cumulus complex cells from the outside of the oocyte prior to performing ICSI procedures).

Providing an aspiration device that may be attached to a finger or a holder, and controlled as described herein is a beneficial way to perform such procedures. The operator is able to retain favorable control of the aspirating volume and placement of the pipette. In addition, the velocity of the aspirate can be readily increased or decreased as desired. This capability is important to insure satisfactory aspiration during micro-manipulation procedures. For example, when aspirating cells, the cells (e.g., oocytes) can readily be aspirated to and from the pipette at a desired rate. In addition, the operator can readily vary the velocity of the aspiration as desired. For example, as recognized by those skilled in the art, it is often desirable to vary (e.g., increase) the velocity of the oocyte during denuding. The aspiration can also be carried out in a manner that minimizes the strain on the digits of the operator.

The device, and its operation, may be better understood upon review of the figures. FIG. 1 illustrates a perspective view of a device 10 suitable for use in aspirating biological sample media, such as biological cells, fluids, or other related media, through a micro-size medical device, such as a pipette. FIG. 2 illustrates a distal end view of the aspiration device of FIG. 1. FIG. 3 illustrates a sectional view of a portion of the pipette aspiration device, taken along line 3-3 of FIG. 2.

One preferred example of such a micro-size pipette is a denuding pipette. In the following discussion, the medical device will often be described simply as a pipette. Those skilled in the art will appreciate that the inventive device has broad application for use in aspirating a wide variety of biological materials in micro-manipulation procedures. The term "pipette" is well known in the medical arts, and particularly in the art of micro-manipulation techniques. One particularly preferred pipette that is useful for many such micro-manipulation techniques is the FLEXIPET® pipette, sold by Cook Medical, of Bloomington, Ind. The FLEXIPET® pipette is formed from polycarbonate, and is generally capable of aspirating volumes from about 0.25 to 3.0 µl. Typically, such pipettes have an inner volume of about 18 to 25 µl. Such pipettes are presently available in various inner diameters, such as 80, 100, 120, 130, 140, 170, 300, and 600 µm, respectively.

As shown in the figures, aspiration device 10 comprises a bulb 12 and a ring member 20. Preferably, bulb 12 and ring member 20 are each formed of an elastomer. Silicone is a particularly preferred elastomer for use in forming the bulb and ring member. It is expected that other elastomers, such as thermoplastic elastomers (TPEs), having elastomeric properties similar to silicone will also be suitable.

Preferably, the bulb and ring member are formed of the same, or of a chemically similar material. Forming the bulb and ring member of the same or a chemically similar material, such as silicone, facilitates engagement therebetween. Silicone is a well-known material for use as a bulb in micro-manipulation techniques, and is preferred for use herein. It also has favorable flexibility characteristics for use as the ring member, and is readily capable of being molded into a desired configuration. Those skilled in the art will appreciate that other materials having similar characteristics may be substituted.

Device 10 can be formed by conventional techniques known in the art, such as by molding. Although many molding techniques known in the art are suitable, one particularly preferred technique is Liquid Injection Molding (LIM). In a LIM process, a suitably-designed mold is provided, and a liquid molding composition is injected into the mold. Liquid silicone is a particularly preferred composition for use in this molding operation. Once again, however, those skilled in the art will appreciate that other liquid compositions capable of being molded to achieve the desired properties of device 10 can be substituted.

Alternatively, bulb 12 and ring member 20 can be separately formed by conventional techniques, such as molding (e.g., insert molding, top transfer molding, compression molding), extrusion, etc., and thereafter engaged as shown in the figures by conventional techniques, such as adhesion. To aid in the engagement of an initially separate bulb and ring member, the ring member is preferably provided with a channel along its outer surface for receiving the bulb, whereby the assembled device will have a profile in the nature of the structure shown in FIG. 2. Those skilled in the art can readily fashion other suitable arrangements for engaging the bulb and ring member.

Bulb 12 comprises a generally elongated tubular structure 13 having a closed proximal end 14 and an open distal end 15. Distal end 15 opens into narrow passageway 16, and thereafter into chamber 17. Narrow passageway 16 is dimensioned to allow the proximal end of a pipette to be snugly received therein in well-known fashion. Although the end of the pipette can extend into the chamber 17 if desired, it is preferred that this pipette end does not extend all the way through the passageway and into the chamber, as this would adversely affect the calculated aspiration volume of the pipette. The bulb may be provided with a chamfer 18 at the distal end to allow easy insertion of the pipette.

Aspiration bulbs are well-known in the micro-manipulation art, and detailed description of the structure and operation of such bulbs is not necessary to gain a basic understanding of this feature of the present invention. In one preferred embodiment, passageway 16 may have a length of about 0.25 inch (6.35 mm), and a diameter of about 0.031 inch (0.79 mm). Chamber 17 may have a length of about 0.55 inch (14 mm) and a diameter of 0.068 inch (1.73 mm). Bulb 12 may have a length of 1 inch (25.4 mm) and an outer diameter of about 0.152 inch (3.86 mm). Those skilled in the art will appreciate that suitable aspiration bulbs can be formed in many shapes and sizes, and that the specific dimensions provided above are merely one example of a set of dimensions that is suitable for a particular bulb.

Ring member 20 comprises a generally annular structure 21 that is sized to allow insertion of a digit, such as a finger, of the operator through the center portion 23 of annular structure 21 in well-known fashion. Preferably, annular structure 21 is open at both ends, and includes a void 22 along a small part of its circumference. The presence of void 22 in the annular structure allows the ring member to self-adjust in order to accommodate different finger sizes, and to accommodate different sizes of substrates, such as the container shown in FIGS. 5 and 6. The flexibility of ring member 20 enables it to readily compensate for any such size differences.

Although the ring member described above is preferred, those skilled in that art will appreciate that the ring design as described is merely one example of a possible design, and that other designs are also considered within the scope of the invention. For example, the ring member may be fashioned to include a closed, extended end, in the nature of a thimble. Other alternatives involve use of a condom-like structure, such as a finger cot, that fits over the finger, or a glove-type structure that includes a finger portion that fits over the finger of the operator.

In addition, although preferable, the ring member need not necessarily be formed from a flexible material. Rather, the ring member may be formed of a rigid or semi-rigid composition, such as a rigid plastic, with or without the void. In this embodiment, the bulb would typically be engaged with the ring structure by any suitable engagement means, such as adhesion.

FIG. 4 illustrates one manner of use of the pipette aspiration device 10 of FIG. 1, in this case, for aspirating cells from a dish 44 containing the sample media. In this example, an index finger of the operator is inserted into the center portion of ring member 20, and extends slightly therethrough. For ease of operation, aspiration device 10 is preferably aligned on the index finger in a manner such that bulb 12 is disposed on the side of the finger adjacent to the thumb. This arrangement provides easy and convenient access to the bulb by the operator's thumb (not shown).

Either before, or after, insertion of the ring member 20 onto the index finger of the operator, a pipette 40 is inserted into open distal end 15 of bulb 12. The use of pipettes is well known in the micro-manipulation art, and many suitable pipettes, such as the FLEXIPET® pipette discussed above, are commercially available. Those skilled in the art can readily select an appropriate pipette for a particular technique. Preferably, the proximal end of the pipette extends into passageway 16, but does not extend further into chamber 17 (FIG. 1).

In operation, the operator will typically use his or her thumb to compress the bulb against the index finger prior to the pipette contacting the sample media, thereby expelling fluid from the chamber. The device is now ready for aspiration of sample media. The tip of the pipette is inserted into the sample media, and the operator slowly releases the compression exerted on the bulb by his/her thumb. The suction, or aspirating, force created upon releasing the compression draws sample media into the pipette. The degree at which the compression on the bulb is released may be controlled by the operator to control the amount of aspiration desired, and therefore, the amount of sample media drawn into the pipette.

Utilizing the aspiration device 10 on the finger of the user as shown and described provides the operator with very favorable control of the aspiration procedure, and allows the operator to favorably control the aspiration volume. In addition, the arrangement allows freedom of movement of the finger for satisfactory placement of the pipette tip in the sample media. Although in theory any combination of digits of the operator may be utilized for placement of the ring member, and compression of the bulb, it is believed in most instances that use of the index finger/thumb combination as described will be most convenient, and provides very favorable control to the operator. Additionally, use of the aspiration device in this manner minimizes repetitive strain on the operator.

Figure 5:
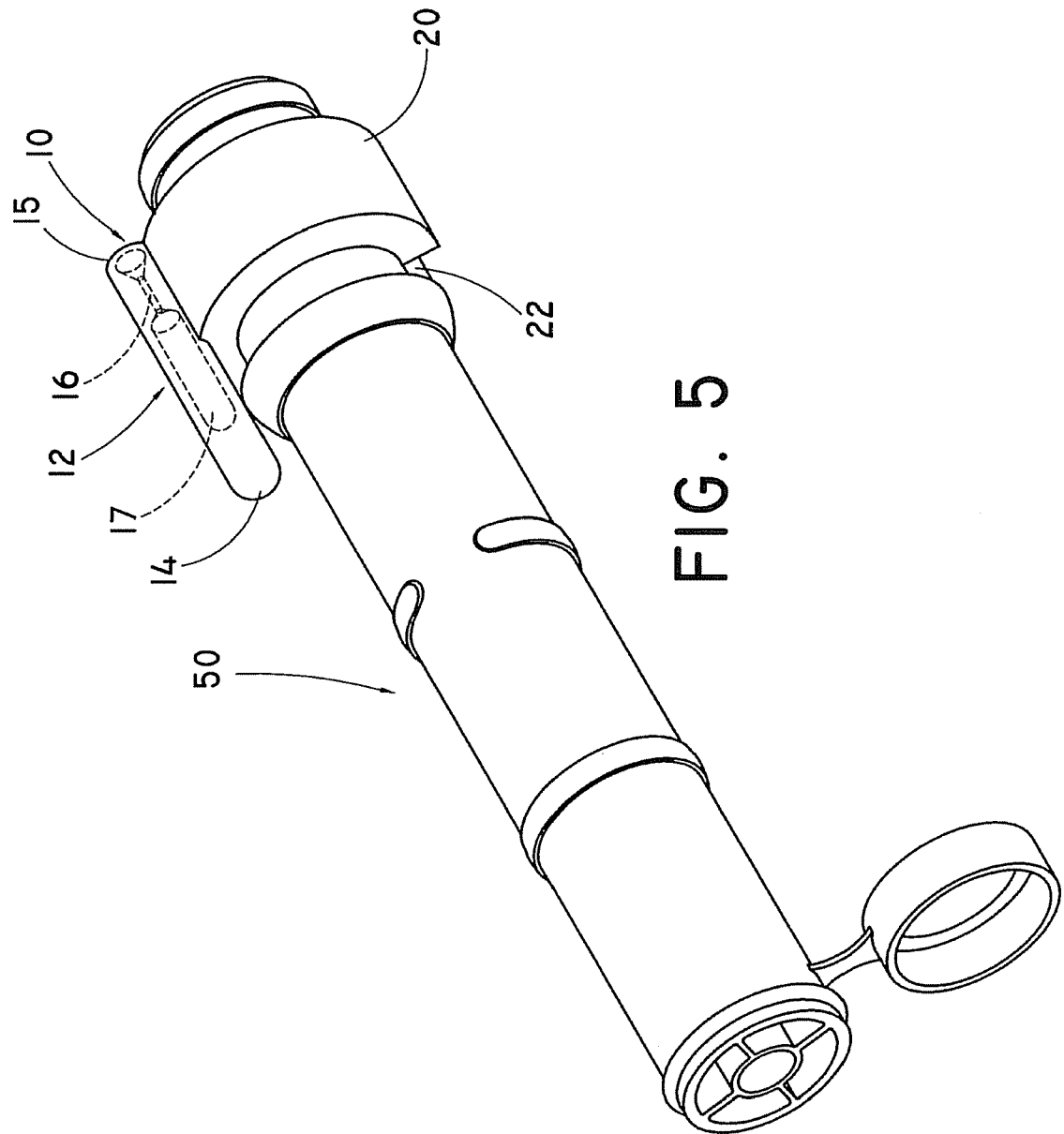
FIG. 5 is a perspective view of a holder for aspiration pipettes, illustrating engagement of the pipette aspiration device to the holder.
Figure 6:
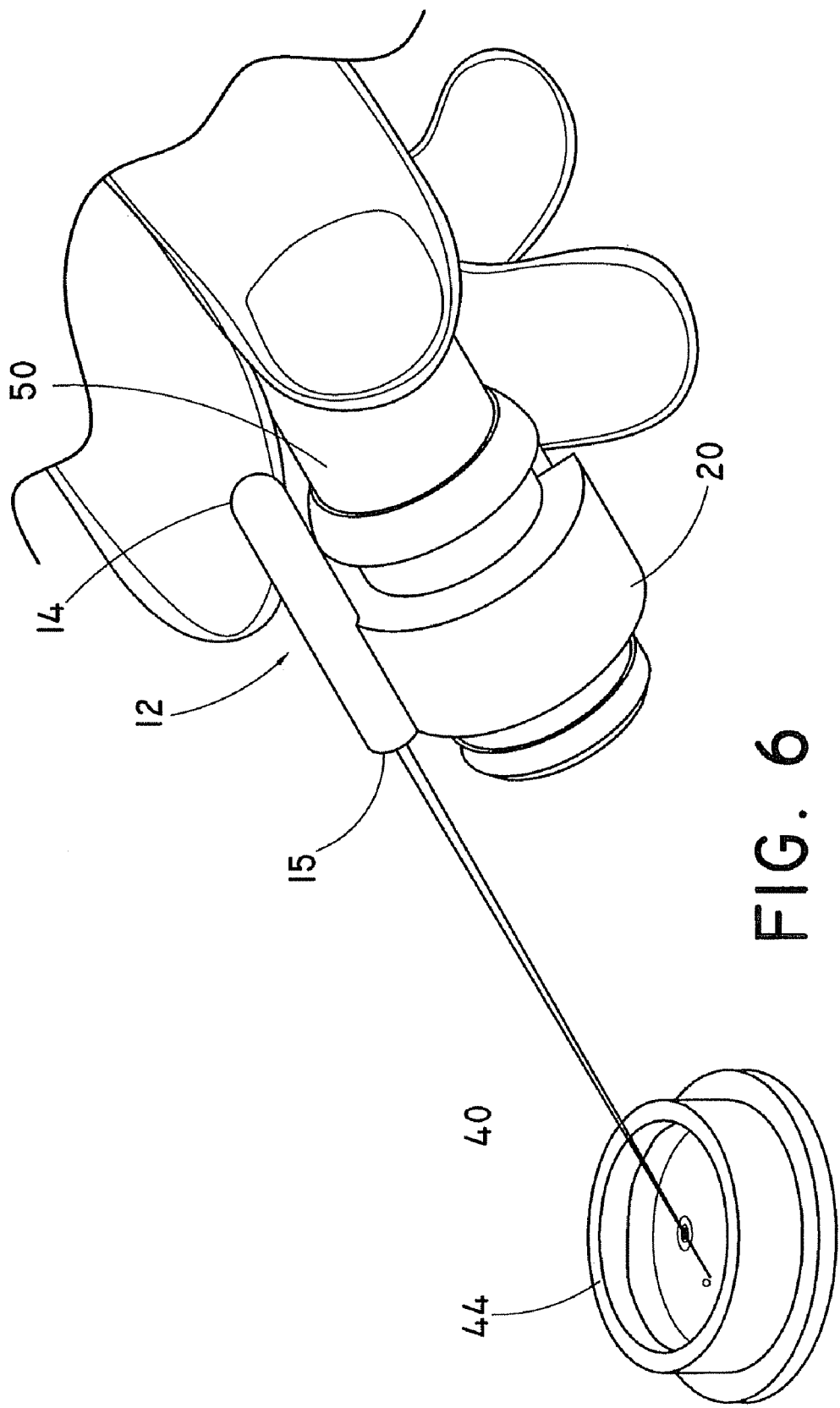
FIG. 6 is a view illustrating use of the pipette aspiration device when the device is engaged with the holder of FIG. 5.

FIGS. 5 and 6 illustrate an alternative manner of use of the inventive device. According to this manner of use, the aspiration tool 10 is affixed to a substrate that is capable of being easily grasped by the operator. In the non-limiting embodiment of FIGS. 5 and 6, the substrate comprises a container, or holder, 50 of a type that may be used to store the pipettes prior to use. The versatility of ring member 20, provided by the flexible nature of the ring member itself and/or the presence of the optional void 22, enables the ring member to be readily fitted for use with holders of different sizes. In FIGS. 5 and 6, the aspiration device 10 is engaged around an end of a holder as described in U.S. Patent Publication No. 2007/0125675, incorporated by reference herein.

The holder 50 described in the incorporated-by-reference patent publication is particularly preferred because it is capable of housing the pipettes in a clean, sterile and undamaged state. The holder also provides a controlled mechanism for safely dispensing a single pipette at a time, and in the substantial absence of contamination. By combining the holder with the aspiration device 10, a very versatile and convenient assembly can be provided.

As illustrated in FIG. 6, when aspiration device 10 is affixed to holder 50, the holder is grasped by the operator. The entire assembly may then be readily aligned for use in the same manner as when the aspiration device is applied directly to the finger of the operator (FIG. 4). The bulb may be compressed by either the finger or the thumb of the operator. Once again, it is preferred that the bulb is compressed by a digit, for example, the thumb, of the operator on the same hand that is utilized to grasp the aspiration device.

Although FIGS. 5 and 6 illustrate affixation of the aspiration device 10 to pipette container, or holder, 50, those skilled in the art will appreciate that the aspiration device may alternatively be affixed or otherwise engaged with any suitable substrate capable of being conveniently grasped by the operator for use as described herein. Preferably, the substrate will include a generally cylindrical outer surface capable of being snugly received within the opening 23 of the ring member, in the same manner in which the finger is receivable in the opening. However, although most preferred, this configuration is not necessarily required in all instances. For example, the substrate may have other outer geometrical configurations, such as square. In such instances, the inner perimeter of the ring member may be configured, if desired, to correspond to the outer configuration of the substrate.

It is therefore intended that the foregoing detailed description be regarded as illustrative rather than limiting, and that it be understood that it is the following claims, including all equivalents, that are intended to define the spirit and scope of this invention.

The invention claimed is:

1. A device for use in aspirating sample media into a pipette, comprising:
 a ring member having an opening sized for receiving a digit of an operator or a substrate capable of being grasped by a hand of the operator; and
 an aspirating bulb engaged with an outer surface of said ring member, said aspirating bulb having an open end with an end of the pipette situated therein, and having a closed end, said aspirating bulb including a compressible chamber capable of creating a suction force suitable for aspirating said sample media into said pipette, said aspirating bulb being oriented along said ring member such that said chamber is compressible by a digit on the same hand of the operator as the digit receivable in the ring member or on the hand that grasps the substrate.

2. The device of claim 1, wherein said ring member outer surface includes a channel formed therealong, and wherein said aspirating bulb is received in said channel.

3. The device of claim 1, wherein said aspirating bulb includes a narrow passageway in communication with said open end, said narrow passageway opening into said chamber.

4. The device of claim 1, wherein said ring member and said aspirating bulb comprise elastomers.

5. The device of claim 1, wherein said ring member and said aspirating bulb comprise silicone.

6. The device of claim 1, wherein said ring member and said aspirating bulb comprise an integrally-molded structure.

7. The device of claim 1, wherein said ring member has a circumference, and includes a void along a portion of said circumference.

8. The device of claim 1, wherein said ring member opening is sized to receive an index finger of the operator, and the aspirating bulb is oriented on the device such that the chamber is compressible by the thumb on said hand.

9. The device of claim 1, wherein said ring member opening is sized to receive said substrate, said substrate comprising a container for said pipette.

* * * * *